(12) United States Patent
Hildreth et al.

(10) Patent No.: US 10,288,638 B2
(45) Date of Patent: May 14, 2019

(54) NON-CONTACT SYSTEMS AND METHODS TO LOCATE SHARP TIPS

(71) Applicants: ARIZONA BOARD OF REGENTS ON BEHALF OF ARIZONA STATE UNIVERSITY, Scottsdale, AZ (US); Aric Sanders, Broomfield, CO (US)

(72) Inventors: Owen Hildreth, Tempe, AZ (US); Aric Sanders, Broomfield, CO (US); Galen Arnold, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 237 days.

(21) Appl. No.: 15/356,057

(22) Filed: Nov. 18, 2016

(65) Prior Publication Data

US 2017/0146560 A1   May 25, 2017

Related U.S. Application Data

(60) Provisional application No. 62/257,388, filed on Nov. 19, 2015, provisional application No. 62/276,448, filed on Jan. 8, 2016.

(51) Int. Cl.
*G01B 11/00* (2006.01)
*G01N 35/10* (2006.01)
(52) U.S. Cl.
CPC ........ *G01N 35/1011* (2013.01); *G01B 11/002* (2013.01); *G01N 2035/1013* (2013.01); *G01N 2035/1039* (2013.01)

(58) Field of Classification Search
CPC .......... G01N 35/1011; G01N 35/1013; G01N 2035/1039; G01N 2035/1041;
(Continued)

(56) References Cited

U.S. PATENT DOCUMENTS 7,319,528 B2    1/2008  Hidaka
2007/0227271 A1* 10/2007 Curtis .................... B01L 3/021
                                                    73/864.14

(Continued)

FOREIGN PATENT DOCUMENTS

WO        2012041522       4/2012

OTHER PUBLICATIONS

King et al., "Ultrasound Atomic Force Microscopy: Atomic-Scale Stability and Registration in Ambient Conditions," Nano Letters, Jan. 27, 2009, vol. 9, No. 4, 1451-1456, American Chemical Society 2009.

(Continued)

*Primary Examiner* — Robert R Raevis
(74) *Attorney, Agent, or Firm* — Michael Best & Friedrich LLP (57) ABSTRACT

Systems and methods are described for a non-contact method for positioning a tip of an object. A light beam of known dimensions is projected and a position of the tip of the object relative to the light beam is adjusted. Light scatter indicative of the tip of the object being positioned within the dimensions of the light beam is detected and a position of the tip of the object is determined based at least in part on the known dimensions of the light beam and the detected light scatter.

20 Claims, 6 Drawing Sheets

(58) Field of Classification Search
CPC .......... G01N 2035/1013; G01B 11/002; G01B 11/005; G01B 11/007; G01B 11/02–11/046
USPC ..... 73/1.79, 1.81, 864.25; 356/614, 634–640
See application file for complete search history.

(56) References Cited

U.S. PATENT DOCUMENTS

2011/0035848 A1    2/2011  Perkins et al.
2017/0219621 A1*  8/2017  Andreev ............... G01P 15/123

OTHER PUBLICATIONS

An et al., "High-Resolution Printing of 3D Structure Using an Electrohydrodynamic Inkjet with Multiple Functional Inks," Jun. 19, 2015, Adv. Mater. 2015, 27, 4322-4328, Wiley-VCH.

* cited by examiner

NON-CONTACT SYSTEMS AND METHODS TO LOCATE SHARP TIPS

RELATED APPLICATIONS

This application claims the benefit of U.S. Provisional Patent Application No. 62/257,388, filed on Nov. 19, 2015, and U.S. Provisional Patent Application No. 62/276,448, filed Jan. 8, 2016, the entire contents of both of which are incorporated herein by reference.

BACKGROUND

The present invention relates to systems and methods for determining a position of a sharp tip of an object (such as, for example, a micropipette tip) and for controllably adjusting the position of the sharp tip.

SUMMARY

In one embodiment, the invention provides a non-contact method for positioning a tip of an object. A light beam of known dimensions is projected and a position of the tip of the object relative to the light beam is adjusted. Light scatter indicative of the tip of the object being positioned within the dimensions of the light beam is detected and a position of the tip of the object is determined based at least in part on the known dimensions of the light beam and the detected light scatter.

In another embodiment, the invention provides a system for positioning a tip of an object. The system includes a light source, a positioning stage, a camera, and a controller. The light source is configured to project a light beam of known dimensions. The positioning stage is configured to controllably adjust a position of the tip of the object relative to the light beam. The camera is positioned with a field of view including at least a portion of the light beam. The controller is configured to operate the positioning stage to adjust a position of the tip of the object relative to the light beam and to analyze a sequence of images received from the camera to detect light scatter indicative of the tip of the object being positioned within the dimensions of the light beam. The controller then determines a position of the tip of the object based at least in part on the known dimensions of the light beam and the detected light scatter.

In yet another embodiment, the invention provides a method of positioning a tip of an object. A light beam of known dimensions is projected proximal to a substrate surface. A positioning stage is operated to controllably adjust a position of the tip relative to the light beam such that the tip crosses a boundary of the light beam a plurality of times. An electronic processor analyzes images captured by a camera positioned with a field of view including at least a portion of the light beam to detect light scatter indicative of the tip being positioned within the dimensions of the dimensions of the light beam. The electronic processor detects that the tip crosses a boundary of the light beam when the light scatter is present in a current image captured by the camera and the light scatter is absent in a previous image captured by the camera. The electronic processor also detect that the tip crosses the boundary of the light beam when the light scatter is absent in the current image captured by the camera and the light scatter is present in the previous image captured by the camera. The dimensions of the light beam are mapped relative to the tip based on a plurality of points each determined based on a three-dimensional position setting of the positioning stage when the electronic processor detects that the tip crosses the boundary of the light beam. A position of the tip relative to the light beam is determined based on the mapped dimensions of the light beam relative to the tip. A position of the tip relative to the substrate is then determined based on the determined position of the tip relative to the light beam and a determined position of the light beam relative to the substrate. Finally, the position of the tip is adjusted based on the determined position of the tip relative to the substrate.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
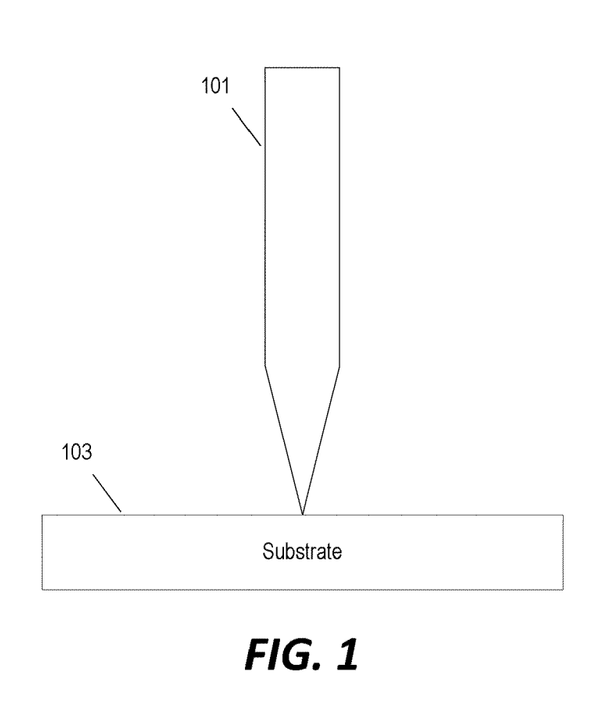
FIG. 1 is a schematic view of a contact-based method for determining a position of a micropipette tip.

Some processes require precisely determining a position/location of a small sharp-tipped object. For example, in some ElectroHydroDynamic (EHD) printing processes, the tip of a small micropipette (e.g., less than 1 µm in diameter) is controllably placed within 3-5 µm of a substrate surface with an accuracy of 200 nm or less. FIG. 1 illustrates one possible mechanism for precisely determining the location of a small sharp-tipped object such as the tip of a micropipette for EHD printing. The tip 101 is coated with a conductive layer (e.g., gold) and a resistance between the tip 101 and a flat conductive substrate 103 is monitored as tip 101 is brought towards the substrate 103. When the resistance drops below a certain threshold (e.g., 1000Ω), the tip 101 and the substrate 103 are assumed to be in contact and, accordingly, the position of the tip 101 relative to the substrate 103 is known for a single axis (e.g., z(height)=0).

However, the process illustrated in FIG. 1 poses a number of limitations. First, the small sharp tip might be damaged when moved into contact with the substrate surface. The risk of damage might be somewhat reduced by slowing the speed at which the tip 101 is moved towards the substrate 103. However, slowing the speed further slows the amount of time required to determine the position of the tip 101 and does not completely eliminate the risk of damage to the tip 101 caused by contact with the substrate 103. Second, because both the substrate and the tip must be conductive, the substrate and material options are limited. Monitoring an electrical resistance also requires the use of expensive electrical equipment (e.g., a multimeter).

Figure 2:
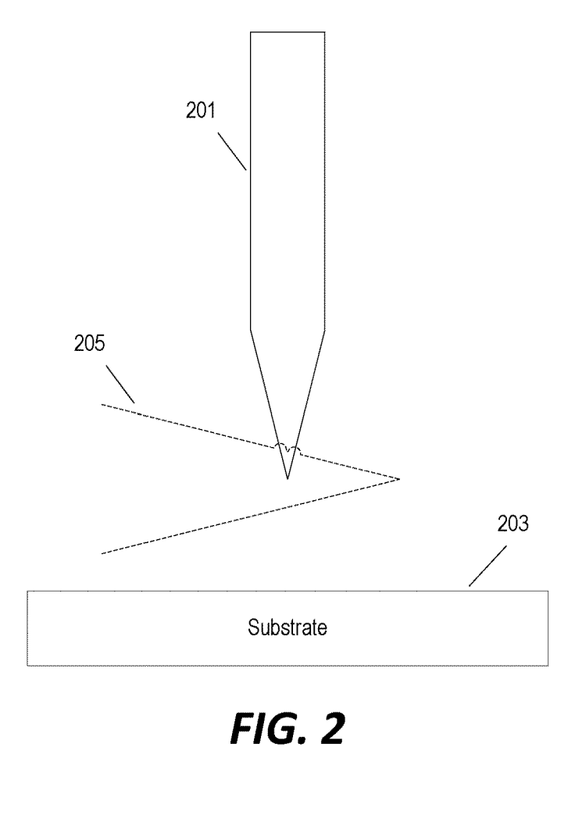
FIG. 2 is a schematic view of a non-contact method for determining a position of a micropipette tip.

FIG. 2 illustrates an alternative process for determining a location of a sharp tip of an object that does not require contact between the sharp tip and any other object. In the example of FIG. 2, the tip of a micropipette 201 is again lowered towards a substrate 203. A beam of light—in this case, a light cone 205—is projected into the space between the micropipette 201 and the substrate 203. As the micropipette 201 is lowered towards the substrate 203, the tip of the micropipette 201 will eventually enter the light cone 205 causing light scatter. Therefore, the position of the tip of the micropipette 201 relative to the light cone 205 can be determined at the time when the light scatter is first detected. If the position of the light cone 205 relative to the substrate 203 is known, then the position of the tip of the micropipette 201 can be determine when the light scatter is first detected. Not only does the method of FIG. 2 not require contact between the micropipette 201 and the substrate 203, but, because of the dimensional shape of the light beam (e.g., light cone 205), the position of the tip of the micropipette 201 can be determined on two or, in some implementations, three axes as discussed in further detail below.

Figure 3:
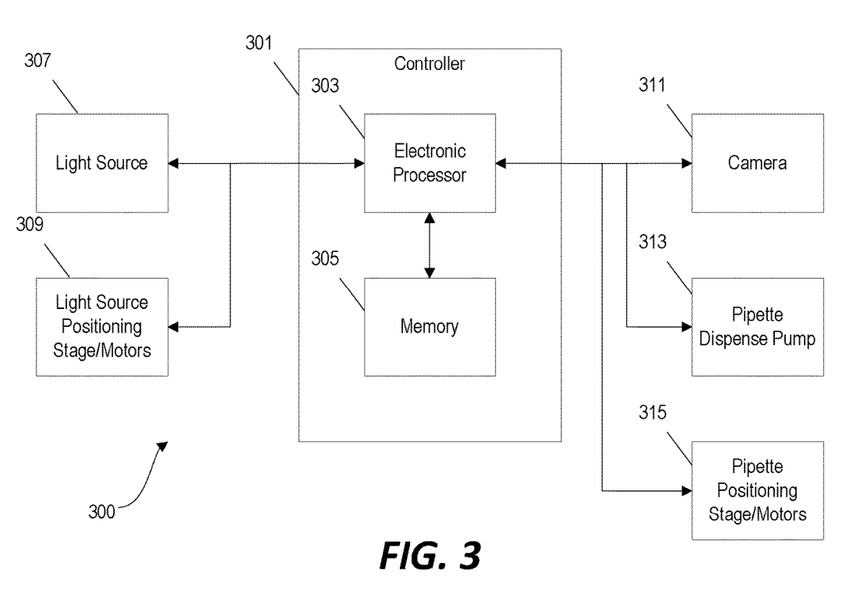
FIG. 3 is a block diagram of a system for determining a position of a micropipette tip using the non-contact method of FIG. 2.

FIG. 3 illustrates an example of a system 300 for positioning a micropipette and for determining the location of a micropipette using the process illustrated in FIG. 2. The system 300 includes a controller 301 configured to monitor and control various other components of the system 300. In the example of FIG. 3, the controller 301 includes an electronic processor 303 and a non-transitory computer-readable memory 305. The memory 305 stores instructions that are accessed and executed by the electronic processor 303 to provide the operation and functionality of the system 300 such as described below. However, in other implementation, other types of controllers and control units may be utilized to provide the control functionality such as described below. Similarly, in still other implementations, the system 300 may include multiple controllers, multiple electronic processors, and/or multiple memory modules.

The controller 301 is communicatively coupled to a light source 307 and a light source positioning stage/motor(s) 309. In the examples discussed below, the light source 307 includes a laser. However, in other implementations, the light source 307 can include other forms of light sources including, for example, a light-emitting diode (LED). The light source positioning stage/motor(s) 309 is physically coupled to the light source 307 and is operated by the controller 301 to adjust and control the position of the light source 307.

The controller 301 is also communicatively coupled to a camera 311 that is positioned with a field of view including a location where the pipette tip is expected to cross into the light beam emitted by the light source 307. The controller 301 receives images captured by the camera 311 and processes the received images to detect light scatter indicative of a pipette tip crossing into the light beam as discussed in further detail below. The controller 301 is also communicatively coupled to a pipette dispense pump 313 that operates to controllably expel material (e.g., printing material) through the tip of the pipette and a pipette positioning stage/motor(s) 315 that is physically coupled to the pipette to controllably adjust the position of the pipette tip.

In some implementations, the pipette positioning stage/motor(s) 315 is configured to adjust the position of the pipette tip in only a single axis (e.g., height (z)). However, in other implementations, the pipette positioning stage/motor(s) 315 are configured to adjust the position of the pipette in two or three axes (e.g., height (z), linear position (x), and/or lateral position (y)). Similarly, in various implementations, the light source positioning stage/motor(s) 309 is configured to adjust the position of the light source 307 in one, two, or three axes. However, in still other implementations, the system 300 does not include a light source positioning stage/motor(s) 309 and the light source 307 instead remains stationary relative to the system and stationary relative to a substrate. Accordingly, unless otherwise explicitly specified, some of the examples presented herein that discuss movement of the pipette tip relative to the light source can be implemented by (a) operating the pipette positioning stage/motor(s) 315 to adjust the position of the pipette, (b) operating the light source positioning stage/motor(s) 309 to adjust the position of the light source 307, or (c) operating both the pipette positioning stage/motor(s) 315 and the light source positioning stage/motor(s) 309 to adjust the position of both the light source 307 and the pipette.

Figure 4:
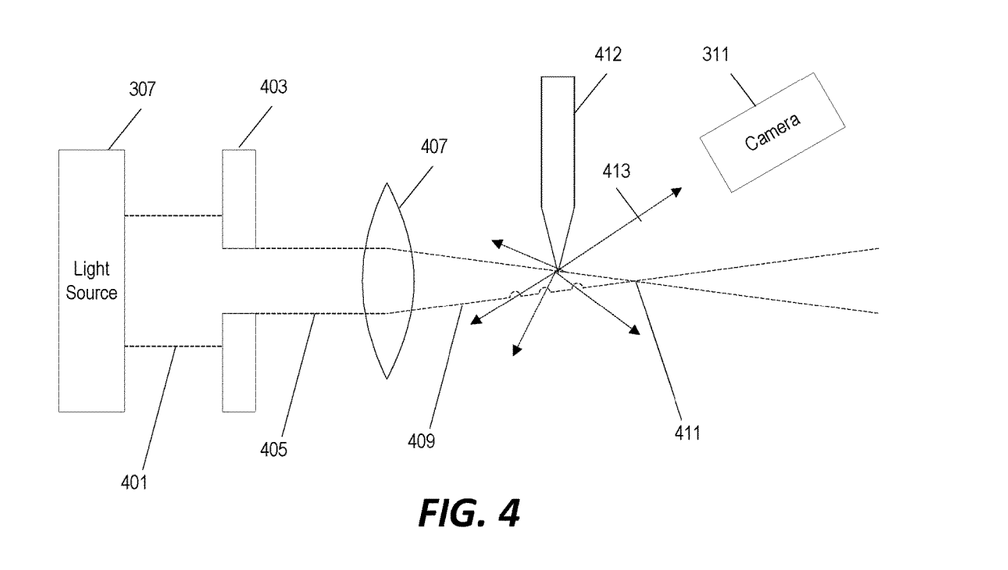
FIG. 4 is a schematic view of the non-contact method for determining the position of a micropipette tip using the system of FIG. 3.

FIG. 4 schematically illustrates an example of the system of FIG. 3 configured to apply the mechanism of FIG. 2. The light source 307 emits a light beam 401 that passes through a circular aperture 403 to produce a light beam 305 of a specific diameter. A focusing lens 407 is positioned in the optical path of the reduced-diameter light beam 405 and forms a light cone 409 that reduces in diameter towards a focal point 411. When a pipette 412 is positioned partially in the optical path of the light cone 409, detectable light scatter 413 is reflected from the surface of the pipette 412. The camera 311 is positioned out of the optical path of the light source and with a field of view that includes a location where the pipette 412 is expected to enter the light cone 409. The camera 311 periodically captures images that are processed by the controller 301 to detect when light scatter 413 is present and, accordingly, when the tip of the pipette 412 is positioned within the light cone 409.

In some implementations where the position of the light source 307 is controllably adjusted by the light source positioning stage/motor(s) 309, the aperture 403 and the focusing lens 407 are fixedly coupled relative to the light source 307 such that the position of the aperture 403 and the focusing lens 407 relative to the light source 307 does not change as the light source 307 is moved and, accordingly, the size and shape of the projected light cone 409 also remains constant. However, in other implementations, the system may be configured to controllably adjust the position of the aperture 403 or the focus lens 407 to controllably adjust the size and shape of the light cone 409.

Furthermore, the system illustrated in FIG. 4 is only one example—other configurations and implementations are possible. For example, some implementations do not include a separate aperture component 403 and the light beam 401 emitted from the light source 307 directly contacts the focus lens 407 without modification. Similarly, other implementations may also include different types of focus lenses 407 to create a light beam of a different size or shape. For example, instead of a focus lens 407 that emits a light cone 409 with a diameter that converges towards a focal point 409, some implementations may include a lens that that emits a light cone with a diameter that continues to increase with the distance between the light beam and the lens. In still other implementations, the system may include no separate focus lens and is instead configured to detect when the tip of the pipette 412 enters a cylindrical light beam emitted by the light source 307.

In the system of FIG. 4, the pipette 412 is gradually lowered as the camera 311 captures images. If the position of the pipette 412 relative to the light source 307 in the lateral (x) and linear (y) directions is known or fixed and the size and shape of the light cone 409 are known, then the position of the tip of the pipette 412 relative to the light source 307 in the vertical (z) direction is also known when the light scatter 413 is first detected in the images captured by the camera 311 as the pipette is lowered towards the light cone 409. Furthermore, if a substrate is positioned below the light cone 409 opposite the pipette 412 and the position of the substrate relative to the light source 307 in the vertical (z) direction is known or fixed, then position of the tip of the pipette 412 relative to the substrate can be determined by the following equation:

$$z^{pipette\ tip\ relative\ to\ substrate} = z^{pipette\ tip\ relative\ to\ light\ source} + z^{light\ source\ relative\ to\ substrate} \quad (1)$$

In some implementations, the system may only need to determine/monitor a distance between a tip of an object (e.g., a pipette) and a substrate surface in a single direction (e.g., a single-axis positioning system). In some such systems, the light source and any associated optics (e.g., focus lens 407) may be configured to project the light beam at a fixed/known position relative to a substrate surface and, accordingly, might not include a light source positioning stage/motor(s) 309. Furthermore, the pipette positioning stage/motor(s) 315 in those systems may be configured to only adjust the position of the pipette 412 in a single direction (e.g., vertical (z)). The system may be configured to position the projected light cone (or another shaped light beam) such that the tip of the pipette 412 will be at its target position relative to the substrate surface when the tip of the pipette 412 first enters the light beam and light scatter is detected. In this type of "single-axis" system, the controller 301 is configured to controllably lower the pipette 412 towards the light cone 409 while processing images received from the camera 311 to detect light scatter 413. The controller 301 is further configured to position the tip of the pipette at a precise location in the single axis direction by stopping movement of the pipette 412 when light scatter 413 is detected by the controller 301 in an image received from the camera 311.

In other implementations (including, for example, EHD printing), the pipette positioning stage/motor(s) 315 are configured to move the pipette in three dimensional space along a lateral axis (x), a linear axis (y), and a vertical axis (z). In some implementations, systems are configured to determine a position of a tip of the pipette (or another structure) by mapping the light cone 409 in three-dimensional space. The position of the tip of the pipette can then be determined relative to the light cone 409 in three dimensions and, if the position of the light cone relative to the substrate is known, the position of the tip of the pipette relative to the substrate can also be determined in three dimension.

Figure 5:
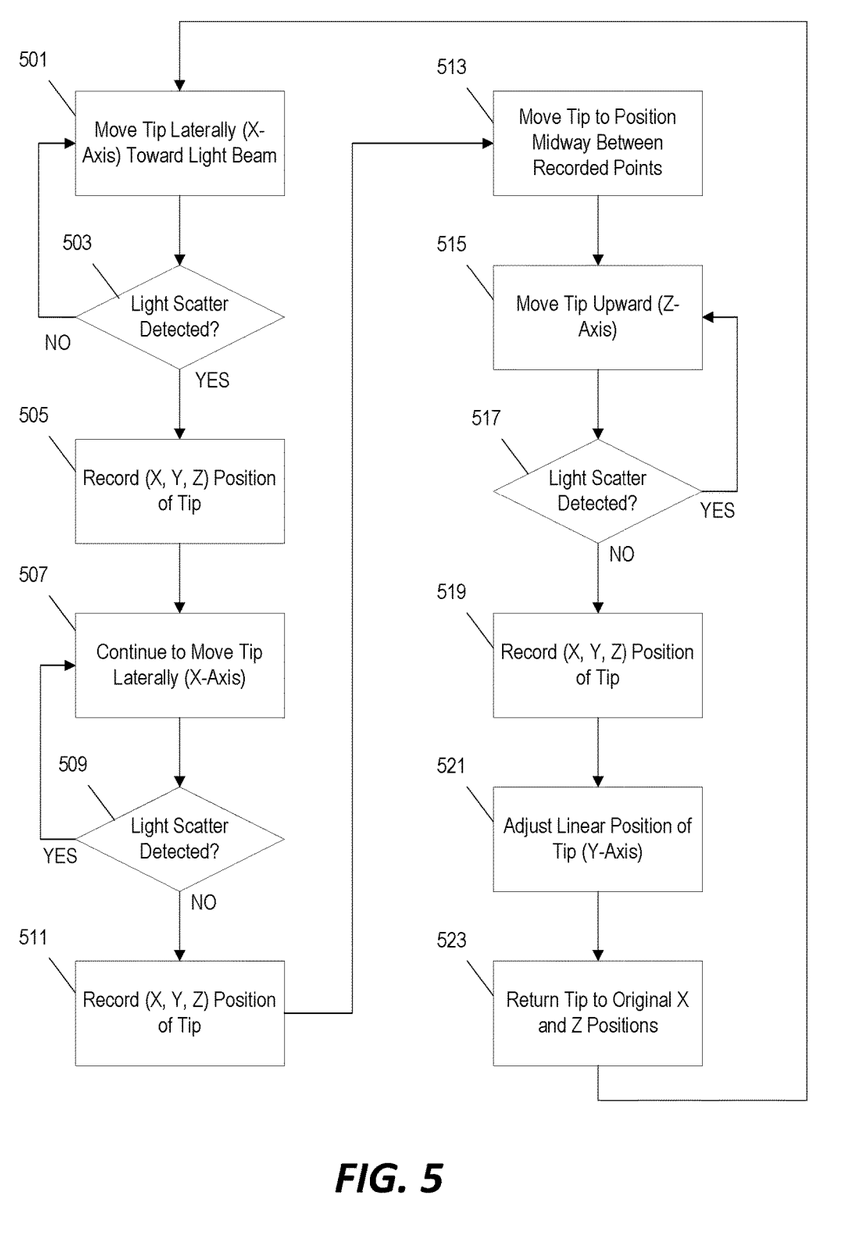
FIG. 5 is a flowchart a method for determining a location of a light beam relative to a micropipette tip using the system of FIGS. 3 and 4.

FIG. 5 illustrates an example of a method for mapping a light cone 409 using the system of FIGS. 3 and 4. First the tip of the pipette is moved laterally (i.e., along the x-axis) toward the light cone (step 501). The controller 301 processes images captured by the camera 311 to determine whether light scatter 413 is present in the captured image (step 503). Because the mapping process begins with the tip positioned outside of the light cone, light scatter 413 should not be detected in the initial images and the controller 501 continues to move the tip laterally until light scatter is detected. Once light scatter 413 is detected in the captured image (step 503), the controller 301 records the position of the pipette tip (x, y, z) based on the position of the controllable stages moving the pipette (i.e., the pipette positioning stage/motor(s) 315) (step 505). The controller 301 then continues to move the tip in the same lateral direction (step 507). Because the tip is now positioned in the light cone 413, light scatter will continue to be present in the captured images until the tip moves out of the light cone 413. Accordingly, the controller 301 continues to process images received from the camera and, upon determining that light scatter is no longer present in the captured image (step 509), the controller 301 again records the position of the tip (step 511).

At this point in the method of FIG. 5, the controller 301 has determined the boundaries of the light cone along a single axis (i.e., the x-axis). To further map the boundaries of the light cone in the same plane, the controller 301 adjusts the position of the tip to a location midway between the two recorded points (step 513) and begins to move the tip upward (i.e., in the z-axis). Because the tip is again positioned in the light cone 413, light scatter will continue to be present in the captured image until the tip moves out of the light cone 413. Accordingly, the controller 301 continues to process images received from the camera and, upon determining that light scatter is no longer present in the captured image (step 517), the controller 301 again records the position of the tip (step 519).

At this point in the method of FIG. 5, the controller 301 has mapped three points on the boundary of the light cone in a single plane. In some implementations, the controller 301 may be configured to map additional points on the boundary of the light cone in the same plane by adjusting the position of the tip in the vertical direction to a different z-axis position between the other detected points. The controller 301 would then again proceed to move the tip of gradually along the x-axis through the cone of light. The x, y, z position of the tip is recorded at the point where light scatter is first detected in an image and where light scatter then ceases to appear in subsequent images providing the location of two additional points on the boundary of the light cone in the same plane.

Returning now to the example of FIG. 5, once a number of points on the boundary of the light cone 413 are identified in the plane, the controller 301 adjusts the linear position of the tip (i.e., along the y-axis) (step 521) and returns the tip to an x-axis and z-axis position outside of the light cone (step 523). The process of FIG. 5 is then repeated to identify points on the boundary of the light cone 413 in a different plane along the y-axis.

Figure 6A:
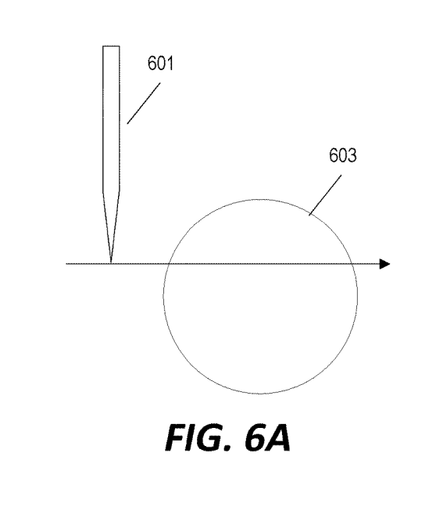
FIGS. 6A through 6E are schematic views of the micropipette tip of the system of FIGS. 3 and 4 at various positions relative to a beam of light during the method of FIG. 5.
Figure 6B:
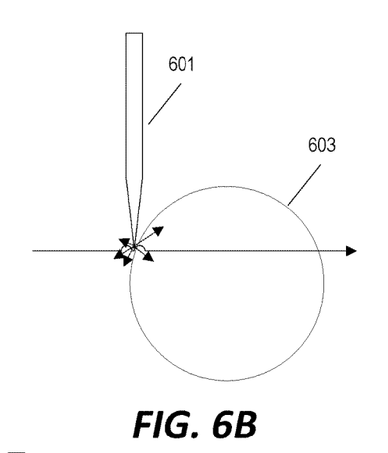
Figure 6C:
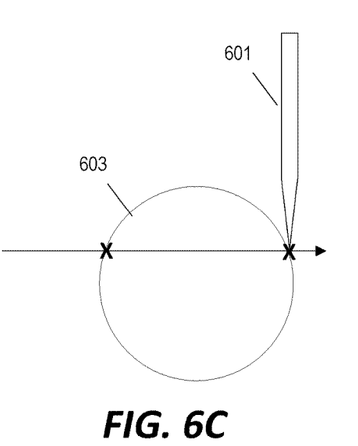
Figure 6D:
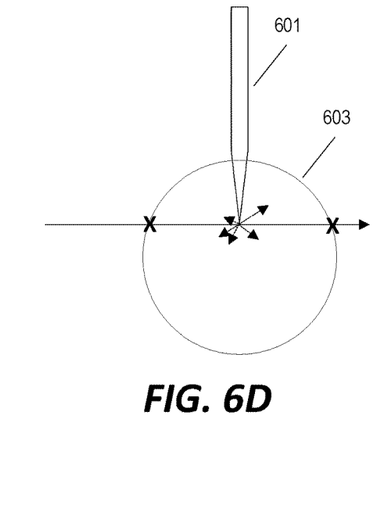
Figure 6E:
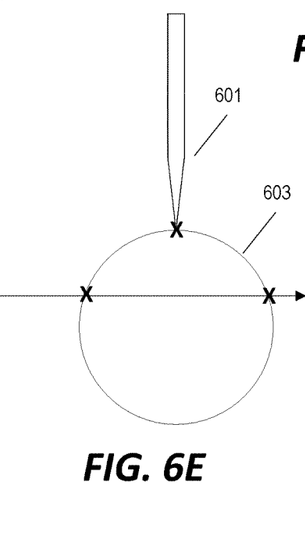

FIGS. 6A through 6E illustrate the method of FIG. 5 graphically each showing a position of a pipette 601 relative to a cross-section of the light cone 603 in a single plane on the y-axis. In FIG. 6A, the tip of the pipette 601 is positioned outside of the light cone 603. The controller moves the pipette laterally along the x-axis until the tip of the pipette 601 enters the light cone 603 causing light scatter as shown in FIG. 6B. This position of the pipette tip is marked (with an "x" in the images of FIGS. 6A through 6E) and the pipette 601 continues to move along the x-axis until the tip of the pipette 601 exits the light cone 603 and light scatter is no longer present as shown in FIG. 6C. This location of the pipette tip is also marked (with an "x" in the images of FIGS. 6A through 6E). The tip of the pipette 601 is then moved in the opposite direction along the x-axis until it reaches a location midway between the two previously marked points as shown in FIG. 6D. Because the tip of the pipette 601 is positioned within the light cone 603, light scatter will be present. The pipette 601 is then moved upward (i.e., along the z-axis) until the tip of the pipette 601 is no longer positioned within the light cone 603 and, accordingly, light scatter is no longer present as shown in FIG. 6E. The position of the pipette tip is marked as a third point on the boundary of the light cone.

Figure 7:
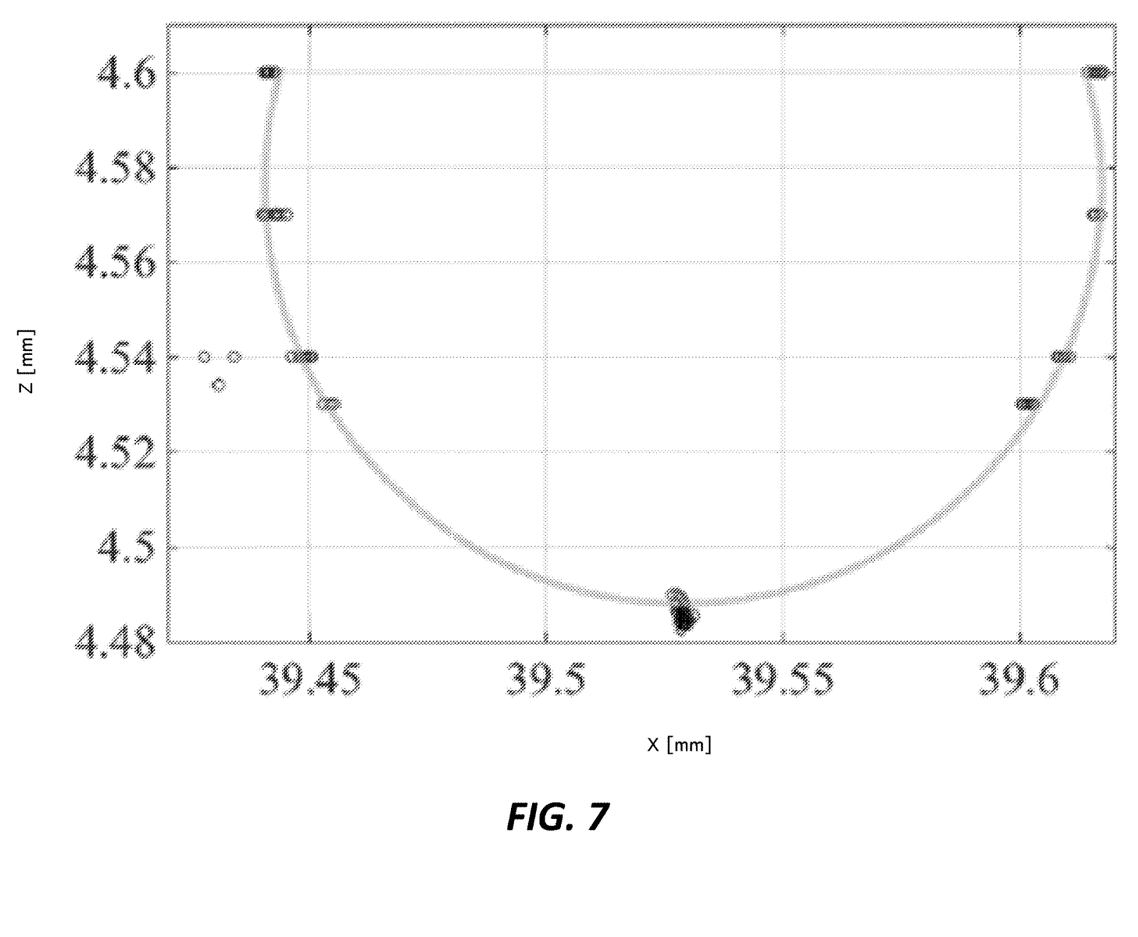
FIG. 7 is a two-dimensional graph of edge points of the beam of light detected by the method of FIG. 5.
Figure 8:
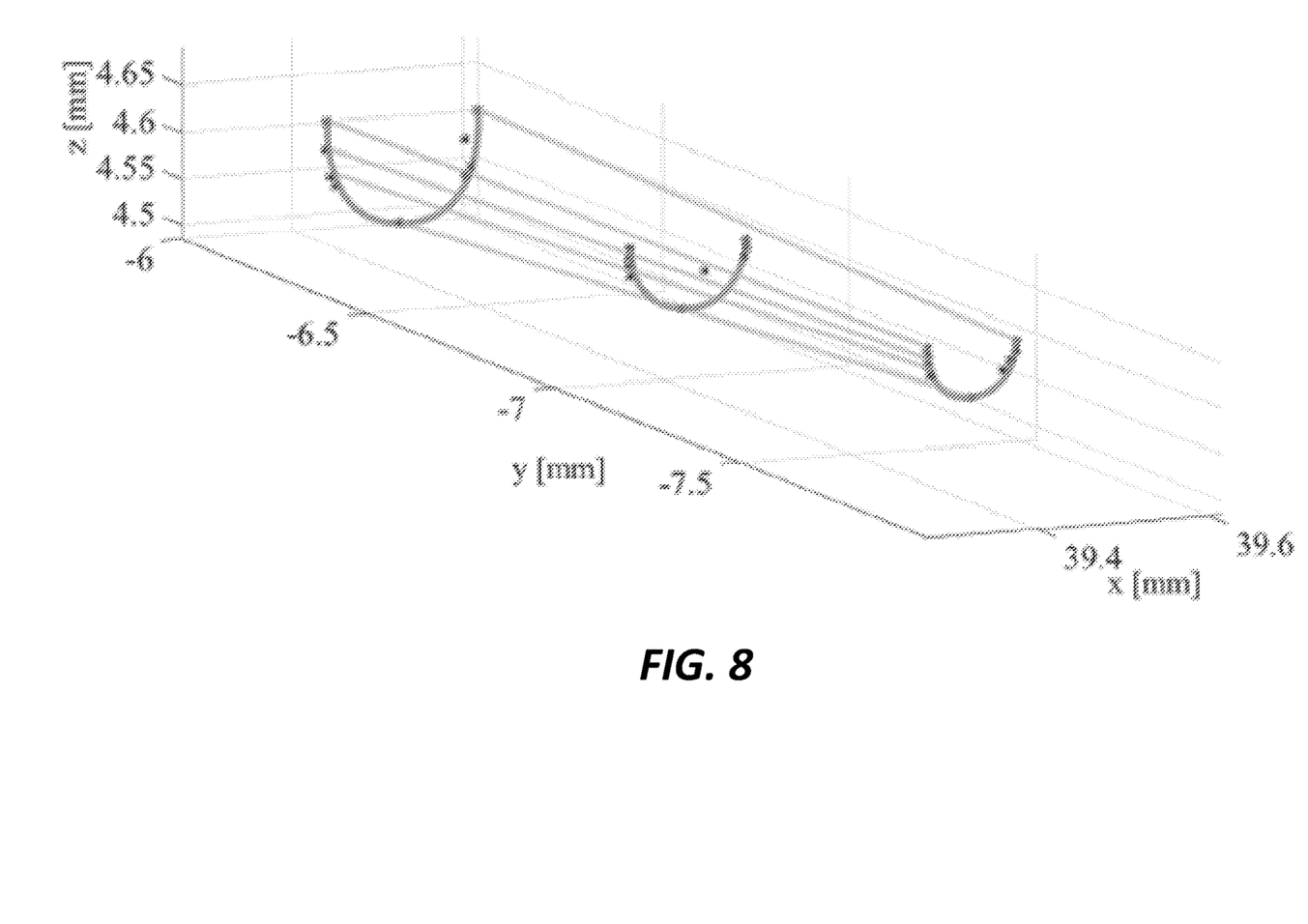
FIG. 8 is a three-dimensional graph of edge points of the beam of light detected by the method of FIG. 5.

To ensure the accuracy of the mapping technique, the controller 301 in some implementations may be configured to repeat the mapping process of FIG. 5 multiple times within a single plane before moving to another location on the y-axis. To further increase the precision of the mapping, the controller 301 may be configured in some implementations to slow the speed at which the pipette is moved as the tip approaches locations where points on the boundary of the light cone were detected during previous iterations of the mapping method. FIG. 7 illustrates an example of a plurality of points detected on the boundary of the light cone after multiple iterations of the mapping technique within a single plane. FIG. 8 shows an example of points detected on the boundary of the light cone in three different planes along the y-axis.

In some implementations, the controller 301 is configured to define the boundary of the light cone in a single plane by adjusting the size and position of a circular shape (or partial circular shape) to best fit the detected data points in each individual plane as shown in FIG. 7. In other embodiments, the controller 301 is configured to define the boundary of the light cone in three-dimensional space by adjusting the size and position of a conical shape (or a partial conical shape) to best fit the detected data points in three-dimensional space as shown in FIG. 8.

The examples discussed above in reference to FIG. 5 and FIGS. 6A through 6E discuss adjusting the position of a pipette relative to a light cone and recording boundary points on the light cone based on the x, y, and z position of the stage/motors used to move the pipette. However, in other implementations (as noted above), the light source and thus the light cone 413 can be controllably moved relative to the pipette and the points on the boundary of the light cone mapped based on the x, y, and z position of the stage/motors used to move the light source. In still other implementations, the camera 311 and/or the controller 301 may be configured to determine the location of the source of light scatter in three-dimensional space based on the images captured by the camera 311.

By mapping the light cone to a small tip of an object such as a pipette, the positioning of the tip is calibrated to the light cone. Using this calibration, the controller 301 is able to determine the position of the tip relative to the light cone as the tip is controllably moved through three-dimensional space. In systems where the light cone is also mapped or otherwise coupled to another reference frame (e.g., a global coordinate frame), the controller 301 is further able to determine a position of the tip in the global coordinate frame.

For example, as discussed above, in some EHD printing systems, the tip of a pipette must be positioned at a specific location relative to a substrate with an accuracy of 200 nm or less. Even if with high-precision motors that are able to move the pipette with sufficient accuracy, the precise location of the tip of the pipette relative to the pipette movement stage may change due to wear of the pipette tip during use or when the pipette is changed/replaced. By mapping the light cone to the pipette tip using a process such as in FIG. 5, the position of the pipette tip can be determined/mapped relative to the light cone. The light cone, being generated by a light source that is coupled to the EHD printing system, is mapped to a global coordinate frame and, therefore, the controller 301 is able to determine the three-dimensional position of the micropipette tip in the global coordinate frame based on the calibration of the position of the pipette tip relative to the light cone using the equation:

$$(x,y,z)^{tip\ to\ global} = (x,y,z)^{tip\ to\ cone} - (x,y,z)^{cone\ to\ global} \quad (2)$$

where $(x, y, z)^{tip\ to\ global}$ is the position of the pipette tip relative to the global coordinate frame, $(x, y, z)^{tip\ to\ cone}$ is the position of the pipette tip relative to the light cone, and $(x, y, z)^{cone\ to\ global}$ is the position of the light cone relative to the global coordinate frame.

If the EHD printing system is calibrated or otherwise configured to determine the position of the substrate relative to the global coordinate frame, then the controller 301 is further able to determine the position of the micropipette tip relative to the substrate using the equation:

$$(x,y,z)^{tip\ to\ substrate} = (x,y,z)^{tip\ to\ global} - (x,y,z)^{substrate\ to\ global} \quad (3)$$

where $(x, y, z)^{tip\ to\ substrate}$ is the position of the pipette tip relative to the substrate surface and $(x, y, z)^{substrate\ to\ global}$ is the position of the substrate surface relative to the global coordinate frame. Alternatively, equations (2) and (3) can be combined to determine the position of the pipette tip relative to the substrate using the equation:

$$(x,y,z)^{tip\ to\ substrate} = [(x,y,z)^{tip\ to\ cone} - (x,y,z)^{cone\ to\ global}] - (x,y,z)^{substrate\ to\ global} \quad (4)$$

Thus, the invention provides, among other things, a method and system for determining a position of a tip of an object without physical contact. Various features and advantages of the invention are set forth in the following claims.

What is claimed is:

1. A non-contact method of positioning a sharp tip of an object, the method comprising:
   projecting a light beam of known dimensions;
   adjusting a position of the tip of the object relative to the light beam;
   detecting light scatter indicative of the sharp tip of the object positioned within the dimensions of the light beam; and
   determining a position of the sharp tip of the object based at least in part on the known dimensions of the light beam and the detected light scatter.

2. The method of claim 1, wherein projecting the light beam of known dimensions includes projecting a light beam through a lens to produce a light cone converging from the lens to a focal point at a known distance from the lens.

3. The method of claim 1, wherein detecting light scatter indicative of the sharp tip of the object entering the dimensions of the light beam includes
   capturing images by a camera positioned with a field of view including at least a portion of the light beam; and
   analyzing, by an electronic processor, the images captured by the camera to determine whether the light scatter is present.

4. The method of claim 3, wherein determining the position of the sharp tip of the object based at least in part on the known dimensions of the light beam and the detected light scatter includes:
   determining that the sharp tip of the object is positioned at a boundary of the light beam when the light scatter is present in a current image received from the camera and the light scatter is not present in a previous image received from the camera.

5. The method of claim 1, wherein adjusting the position of the tip of the object relative to the light beam includes operating a positioning stage to controllably adjust the position of the tip relative to the light beam such that the tip crosses a boundary of the light beam a plurality of times, the method further comprising:
  detecting, by an electronic processor, each time of the plurality of times that the sharp tip crosses the boundary of the light beam based on the detection of light scatter; and
  mapping the boundaries of the light beam relative to the tip based on a plurality of points each determined based on a position setting of the positioning stage.

6. The method of claim 5, wherein detecting, by the electronic processor each time of the plurality of times that the tip crosses the boundary of the light beam based on the detection of the light scatter includes:
  receiving, by the electronic processor, a sequence of images captured by a camera positioned with a field of view including at least a portion of the light beam; and
  detecting, by the electronic processor, that the sharp tip crosses the boundary of the light beam when the light scatter is present in a current image received from the camera and the light scatter is absent in a previous image received from the camera.

7. The method of claim 5, wherein detecting, by the electronic processor each time of the plurality of times that the tip crosses the boundary of the light beam based on the detection of the light scatter includes:
  receiving, by the electronic processor, a sequence of images captured by a camera positioned with a field of view including at least a portion of the light beam; and
  detecting, by the electronic processor, that the sharp tip crosses the boundary of the light beam when the light scatter is absent in a current image received from the camera and the light scatter is present in a previous image received from the camera.

8. The method of claim 5, wherein determining the position of the sharp tip of the object based at least in part on the known dimensions of the light beam and the detected light scatter includes
  determining, by the electronic processor, a position of the sharp tip relative to the light beam based on the mapped boundaries of the light beam relative to the sharp tip; and
  determining, by the electronic processor, a position of the sharp tip relative to a substrate surface based on the determined position of the sharp tip relative to the light beam and a determined position of the light beam relative to the substrate surface,
  the method further comprising adjusting the position of the sharp tip relative to the substrate surface based on the determined position of the sharp tip relative to the substrate surface.

9. The method of claim 5, wherein operating the positioning stage to controllably adjust the position of the tip relative to the light beam includes operating a positioning stage coupled to the object to controllably adjust the position of the sharp tip of the object while the light beam remains stationary.

10. The method of claim 5, wherein operating the positioning stage to controllably adjust the position of the tip relative to the light beam includes operating a positioning stage coupled to a light source projecting the light beam to controllably adjust the position of the light beam while the sharp tip remains stationary.

11. A system for positioning of a tip of an object, the system comprising:
  a light source configured to project a light beam of known dimensions;
  a positioning stage configured to controllably adjust a position of the tip of the object relative to the light source;
  a camera positioned with a field of view including at least a portion of the light beam; and
  a controller configured to
    operate the positioning stage to adjust a position of the tip relative to the light beam,
    analyze a sequence of images received from the camera to detect light scatter indicative of the tip of the object being positioned within the dimensions of the light beam, and
    determine a position of the tip of the object based at least in part on the known dimensions of the light beam and the detected light scatter.

12. The system of claim 11, further comprising a lens positioned in an optical path of the light source to produce a light cone converging from the lens to a focal point at a known distance from the lens.

13. The system of claim 11, wherein the controller is configured to determine the position of the tip of the object based at least in part on the known dimensions of the light beam and the detected light scatter by
  determining that the sharp tip of the object is positioned at a boundary of the light beam when the light scatter is present in a current image received from the camera and the light scatter is not present in a previous image received from the camera.

14. The system of claim 11, wherein the controller is configured to operate the positioning stage to adjust the position of the tip relative to the light beam by operating the positioning stage to controllably adjust a position of the tip relative to the light beam such that the tip crosses a boundary of the light beam a plurality of times, and wherein the controller is further configured to
  detect each time of the plurality of times that the sharp tip crosses the boundary of the light beam based on the detection of light scatter; and
  map the boundaries of the light beam relative to the tip based on a plurality of points each determined based on a position setting of the positioning stage.

15. The system of claim 14, wherein the controller is configured to detect each time that the tip crosses the boundary of the light beam based on the detection of the light scatter by detecting that the tip crosses the boundary of the light beam when the light scatter is present in a current image received from the camera and the light scatter is absent in a previous image received from the camera.

16. The system of claim 14, wherein the controller is configured to detect each time that the tip crosses the boundary of the light beam based on the detection of the light scatter by detecting that the tip crosses the boundary of the light beam when the light scatter is absent in a current image received from the camera and the light scatter is present in a previous image received from the camera.

17. The system of claim 14, wherein the controller is configured to determine the position of the tip of the object based at least in part on the known dimensions of the light beam and the detected light scatter by determining a position of the tip relative to the light beam based on the mapped boundaries of the light beam relative to the tip and a determined position of the light beam relative to the substrate surface, and determining a position of the sharp tip relative to a substrate surface based on the determined position of the sharp tip relative to the light beam and the determined position of the light beam relative to the substrate surface, wherein the controller is further configured to adjust the position of the tip relative to the substrate surface based on the determined position of the sharp tip relative to the substrate surface.

18. The system of claim 17, wherein the positioning stage is coupled to the light source, wherein the controller is configured to controllably adjust the position of the tip relative to the light beam by operating the positioning stage to controllably adjust the position of the light beam while the tip of the object remains stationary, and the system further comprising a second positioning stage selectively couplable to the object, wherein the controller is configured to adjust the position of the tip relative to the substrate surface by operating the second positioning stage to controllably adjust the position of the sharp tip.

19. The system of claim 14, wherein the positioning stage is selectively couplable to the object, and wherein the controller is configured to controllably adjust the position of the tip relative to the light beam by operating the positioning stage to controllably adjust the position of the tip of the object while the light source remains stationary.

20. A non-contact method of positioning a tip of an object, the method comprising:

projecting a light beam of known dimensions proximal to a substrate surface;

operating a positioning stage to controllably adjust a position of the tip relative to the light beam such that the tip crosses a boundary of the light beam a plurality of times;

analyzing, by an electronic processor, images captured by a camera positioned with a field of view including at least a portion of the light beam to detect light scatter indicative of the tip being positioned within the dimensions of the light beam;

detecting, by the electronic processor, that the tip crosses a boundary of the light beam when the light scatter is present in a current image captured by the camera and the light scatter is absent in a previous image captured by the camera;

detecting, by the electronic processor, that the tip crosses the boundary of the light beam when the light scatter is absent in the current image captured by the camera and the light scatter is present in the previous image captured by the camera;

mapping the dimensions of the light beam relative to the tip based on a plurality of points each determined based on a three-dimensional position setting of the positioning stage when the electronic processor detects that the tip crosses the boundary of the light beam;

determining a position of the tip relative to the light beam based on the mapped dimensions of the light beam relative to the tip;

determining a position of the tip relative to the substrate based on the determined position of the tip relative to the light beam and a determined position of the light beam relative to the substrate; and adjusting the position of the tip based on the determined position of the tip relative to the substrate.

* * * * *